US010697968B2

(12) United States Patent
Deng

(10) Patent No.: US 10,697,968 B2
(45) Date of Patent: Jun. 30, 2020

(54) LIPID MARKERS FOR EARLY DIAGNOSIS OF BREAST CANCER

(71) Applicant: Rush University Medical Center, Chicago, IL (US)

(72) Inventor: Youping Deng, Willowbrook, IL (US)

(73) Assignee: Rush University Medical Center, Chicago, IL (US)

(*) Notice: Subject to any disclaimer, the term of this patent is extended or adjusted under 35 U.S.C. 154(b) by 0 days.

(21) Appl. No.: 15/728,735

(22) Filed: Oct. 10, 2017

(65) Prior Publication Data

US 2018/0106808 A1 Apr. 19, 2018

Related U.S. Application Data

(60) Provisional application No. 62/408,410, filed on Oct. 14, 2016.

(51) Int. Cl.
| | |
|---|---|
| G01N 33/574 | (2006.01) |
| G01N 33/92 | (2006.01) |
| A61B 10/00 | (2006.01) |
| G01N 24/00 | (2006.01) |

(52) U.S. Cl.
CPC ... G01N 33/57415 (2013.01); A61B 10/0041 (2013.01); G01N 33/92 (2013.01); G01N 2405/04 (2013.01); G01N 2570/00 (2013.01); G01N 2800/60 (2013.01)

(58) Field of Classification Search
CPC .......... G01N 33/57415; G01N 33/92; G01N 2405/04; G01N 2570/00; G01N 2800/60; A61B 10/0041
See application file for complete search history.

(56) References Cited

U.S. PATENT DOCUMENTS

2013/0109592 A1* 5/2013 Fan .................. G01N 33/57488
506/12

OTHER PUBLICATIONS

Anesi, A. et al.; "A fast liquid chromatography-mass Spectrometry methodology for membrane lipid profiling through hydrophilic interaction liquid chromatography"; Journal of Chromatography A, vol. 1384; 2015; pp. 44-52.

Atahan, K. et al. The value of serumbiomarkers (Bc1, Bc2, Bc3) in the diagnosis of early breast cancer; International Journal of Medical Sciences, vol. 8, Issue 2; Feb. 12, 2011; pp. 148-155.

Bligh, E.G. et al.; "A rapid method of total lipid extraction and purification"; Canadian Journal of Biochemistry and Physiology, vol. 37, No. 8; Aug. 1959; pp. 911-917.

(Continued)

*Primary Examiner* — Jeremy C Flinders
(74) *Attorney, Agent, or Firm* — Barnes & Thornburg LLP

(57) ABSTRACT

Methods for measuring a panel of biomarkers in a subject suspected of having breast cancer are provided. The methods include obtaining a biological sample from the subject and determining a measurement for a panel of biomarkers in the biological sample, the panel comprising at least 5 biomarkers selected from the group comprising LPC(18:3), LPC(20:2), LPC(20:1), LPC(20:0), PC(32:1), PC(34:4), PC(38:3), PC(40:5), PC(40:3), PC(44:11), ePC(32:2), ePC(38:3), C19:1 CE, C19:0 CE, and C20:0 CE, wherein the measurement comprises measuring a level of each of the at least 5 biomarkers.

10 Claims, 5 Drawing Sheets

(56) References Cited

OTHER PUBLICATIONS

Burrell, H.C. et al.; "False-negative breast screening assessment: what lessons can we learn?"; Clinical Radiology, vol. 56, Issue 5; May 1, 2001; pp. 385-358.

Carneiro, A.B. et al.; "Lysophosphatidylcholine triggers TLR2- and TLRr-mediated signaling pathways but counteracts LPS-induced NO synthesis in peritoneal macrophages by inhibiting NF-kappaB translocation and MAPK/ERK phosphorylation"; PloS one 8, No. 9; Sep. 30, 2013; p. e76233; 9 pages.

Chen, X. et al.; "Plasma lipidomics profiling identified lipid biomarkers in distinguishing early stage breast cancer from benign lesions"; Oncotarget, vol. 7, No. 24; May 2, 2016; 10 pages.

Chiarelli, A.M. et al.; "Effectiveness of Screening With Annual Magnetic Resonance Imaging and Mammography: Results of the Initial Screen From the Ontario High Risk Breast Screening Program"; Journal of Clinical Oncology, vol. 32, No. 21; Jul. 20, 2014; pp. 2224-2230.

Cífková, E. et al.; "Lipidomic differentiation between human kidney tumors and surrounding normal tissues using HILIC-HPLC/ESI-MS and multivariate data analysis"; Journal of Chromatography B, 1000; Sep. 1, 2015; pp. 14-21.

Donepudi, M.S. et al.; "Breast cancer statistics and markers"; Journal of Cancer Research and Therapeutics, vol. 10, Issue 3; Jul.-Sep. 2014; pp. 506-511.

Dong, Q. et al.; "Oncogenic action of phospholipase A2 in prostate cancer"; Cancer Letters, vol. 240, Issue 1; Aug. 18, 2006; pp. 9-16.

Fahy, E. et al.; "Update of the Lipid Maps comprehensive classification system for lipids"; Journal of Lipid Research, vol. 50, April Supplement; Apr. 1, 2009; pp. S9-14.

De Gonzalo-Calvo, D. et al.; "Intratumor cholesteryl ester accumulation is associated with human breast cancer proliferation and aggressive potential: a molecular and clinicopathological study"; BMC Cancer, vol. 15, No. 1; Dec. 2015; 460, 14 pages.

Gøtzsche, P.C. et al.; "Screening for breast cancer with mammography"; Cochrane Database of Systematic Reviews, Issue 4; 2011; CD001877; 51 pages.

Gross, R.W. et al.; "Lipidomics at the interface of structure and function in systems biology"; Chemistry & Biology, vol. 18, No. 3; Mar. 25, 2011; pp. 284-291.

Güth, U. et al.; "Tumor size and detection in breast cancer: Self-examination and clinical breast examination are at their limit"; Cancer Detection and Prevention, vol. 32, No. 3; Jan. 1, 2008; pp. 224-228.

Hietanen, E. et al.; "Fatty acid composition of phospholipids and neutral lipids and lipid peroxidation in human breast cancer and lipoma tissue"; downloaded from the internet at https://academic.oup.com/carcin/article-abstract/7/12/1965/2477815 on Mar. 1, 2018;. Carcinogenesis, vol. 7, No. 12; Dec. 1, 1986; pp. 965-1969.

Hilvo, M. et al.; "Novel theranostic opportunities offered by characterization of altered membrane lipid metabolism in breast cancer progression"; Cancer Research, vol. 71, No. 9; May 1, 2011; pp. 3236-3245.

Laye, J.P. et al.; "Phospholipase A2 expression in tumours: A target for therapeutic intervention?"; Drug Discovery Today, vol. 8, No. 15; Aug. 15, 2003; pp. 710-716.

Liu, Y. et al.; "Elevation of sulfatides in ovarian cancer: an integrated transcriptomic and lipidomic analysis including tissue-imaging mass spectrometry"; Molecular Cancer, vol. 9, No. 1; Dec. 2010; p. 186, 13 pages.

Min, H.K. et al.; "Quantitative analysis of urinary phospholipids found in patients with breast cancer by nanoflow liquid chromatography-tandem mass spectrometry: II. Negative ion mode analysis of four phospholipid classes"; Analytical and Bioanalytical Chemistry, vol. 396, No. 3; Feb. 1, 2010; pp. 1273-1280.

Misek, D.E. et al. Protein biomarkers for the early detection of breast cancer. International Journal of Proteomics, vol. 2011; 2011; Article ID 343582; 9 pages.

Misra, S. et al.; "Naturally occurring ether-linked phosphatidylcholine activates phosphatidylinositol 3-kinase and stimulates cell growth"; Journal of Cellular Biochemistry, vol. 55, No. 1; May 1, 1994; pp. 146-153.

Molina, R. et al.; "Tumor markers in breast cancer—European Group on Tumor Markers recommendations"; Tumor Biology, vol. 26; Oct. 25, 2005; pp. 281-293.

Monet, M. et al.; "Lysophospholipids stimulate prostate cancer cell migration via TRPV2 channel activation"; Biochimica et biophysica acta. Mar. 3, 2009; 1793 pp. 528-539.

Morris, E. et al.; "Implications of Overdiagnosis: Impact on Screening Mammography Practices"; Population Health Management, vol. 18, Supplement 1; Sep. 1, 2015; pp. S3-S11.

Morrow, M. et al.; "MRI for breast cancer screening, diagnosis, and treatment"; Lancet, vol. 378; Nov. 19, 2011; pp. 1804-1811.

Qin, X. et al.; "Lysophosphatidylcholine perpetuates macrophage polarization toward classically activated phenotype in inflammation"; Cellular Immunology, vol. 289; May 1, 2014 pp. 185-190.

Qiu, Y. et al. "W. Mass spectrometry-based quantitative metabolomics revealed a distinct lipid profile in breast cancer patients"; International Journal of Molecular Sciences, vol. 14, No. 4; Apr. 12, 2013; pp. 8047-8061.

Rosenberg, R.D. et al.; "Performance benchmarks for screening mammography"; Radiology, vol. 241, No. 1; Oct. 2006; pp. 55-66.

Sekas, G. et al.; "Origin of plasma lysophosphatidylcholine: evidence for direct hepatic secretion in the rat"; The Journal of Laboratory and Clinical Medicine, vol. 105, No. 2; Feb. 1985; pp. 190-194.

Siegel, R.L. et al.; "Cancer statistics"; CA A Cancer Journal for Clinicians, vol. 65, No. 1; Jan./Feb. 2015; pp. 5-29.

Taguchi, R. et al.; "Focused lipidomics by tandem mass spectrometry"; Journal of Chromatography B, vol. 823; Jun. 2005; pp. 26-36.

Tan, M. et al.; "Lysophosphatidylcholine activates a novel PKD2-medicated signaling pathway that controls monocyte migration"; Arteriosclerosis, Thrombosis, and Vascular Biology, vol. 29, No. 9; Sep. 2009; pp. 1376-1382.

Taylor, L.A. et al.; "Plasma lyso-phosphatidylcholine concentration is decreased in cancer patients with weight loss and activated inflammatory status"; Lipids in Health and Disease, vol. 6; Jul. 10, 2007; 8 pages.

Wuhnaqimuge, et al.; "Lysophosphatidylcholine enhances NGF-induced MAK and AKt signals through the extracellular domain of TrkA in PC12 cells"; FEBS Open Bio, vol. 3; Jan. 1, 2013; pp. 243-251.

Yahalom, J.; "Evidence-based breast cancer screening guidelines for women who received chest irradiation at a young age"; Journal of Clinical Oncology, vol. 31, No. 18; Jun. 20, 2013; pp. 2240-2242.

Yamashita, S. et al.; "Increased expression of membrane-associated phospholipase A2 shows malignant potential of human breast cancer cells"; Cancer, vol. 71, No. 10; May 15, 1993; pp. 3058-3064.

Yang, K. et al.; "Multidimensional mass spectrometry-based shotgun lipidomics analysis of vinyl ether diglycerides"; Analytical and Bioanalytical Chemistry, vol. 407, No. 17; Jul. 1, 2015; pp. 5199-5210.

Yang, L. et al.; "Comprehensive lipid profiling of plasma in patients with benign breast tumor and breast cancer reveals novel biomarkers"; Analytical and Bioanalytical Chemistry, vol. 407, No. 17; Jul. 1, 2015; pp. 5065-5077.

You, J. et al.; "Analysis of Phosphatidylcholines (PCs) and Lysophosphatidylcholines (LysoPCs) in Metastasis of Breast Cancer Cells"; Progress in Biochemistry and Biophysics, vol. 42, No. 6; 2015; pp. 563-573.

Zhang, G.M. et al.; "Serum lipid profiles: novel biomarkers predicting advanced prostate cancer in patients receiving radical prostatectomy"; Asian Journal of Andrology, vol. 17, No. 2; 2015; pp. 239-244.

Zhang, T. et al.; "Development of a mass-spectrometry-based lipidomics platform for the profiling of phospholipids and sphingolipids in brain tissues"; Analytical and Bioanalytical Chemistry, vol. 407, No. 21; Jun. 2015; pp. 6543-6555.

(56) References Cited

OTHER PUBLICATIONS

Zhou, X. et al.; "Identification of plasma lipid biomarkers for prostate cancer by lipidomics and bioinformatics"; PloS One; Nov. 12, 2012; 11 pages.

* cited by examiner

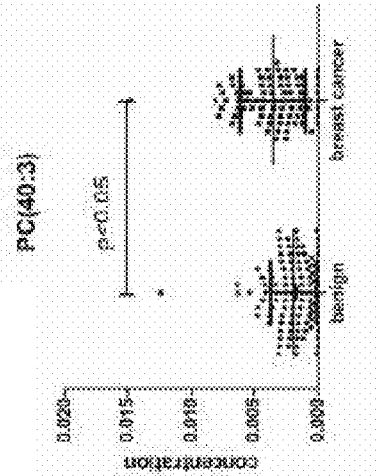
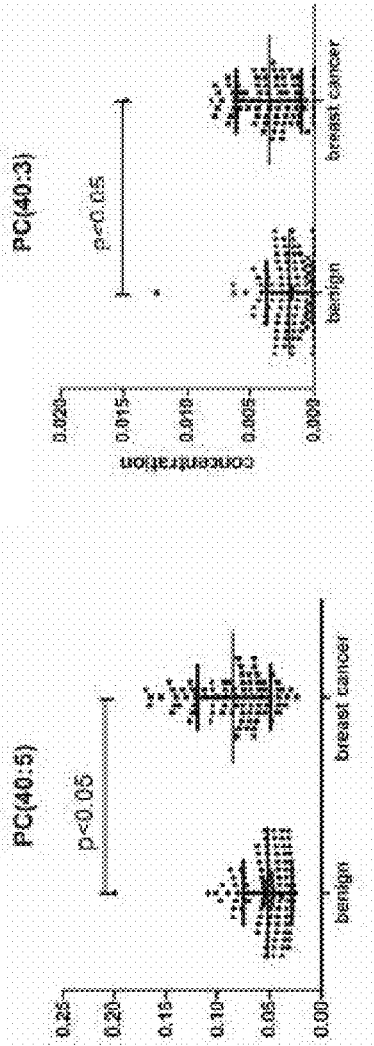
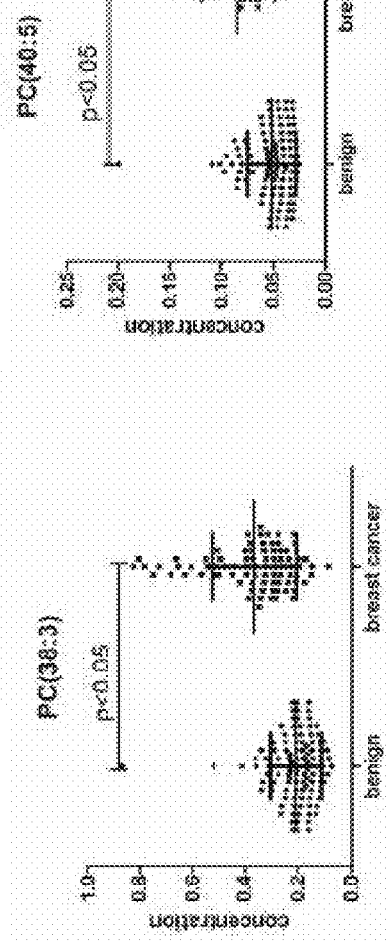
FIG. 2G
FIG. 2H
FIG. 2I
FIG. 2J
FIG. 2K
FIG. 2L
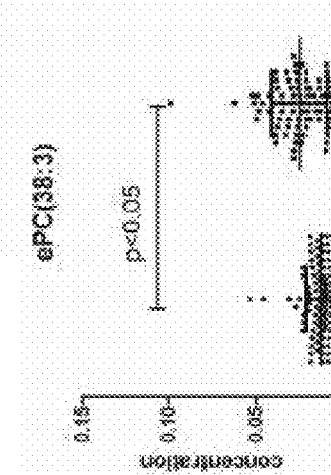
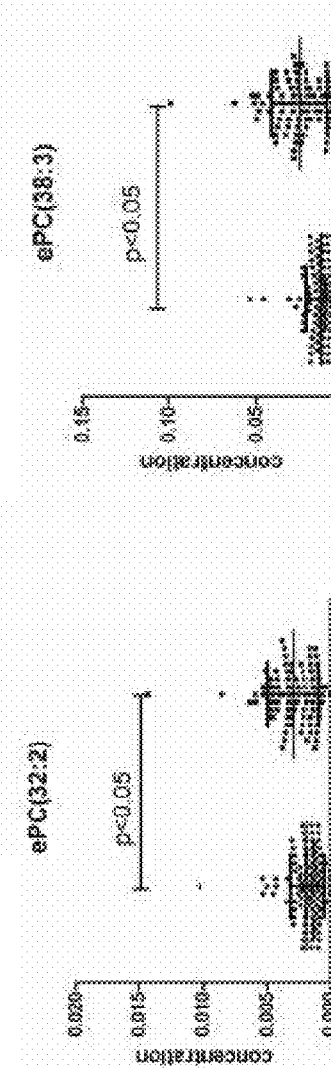
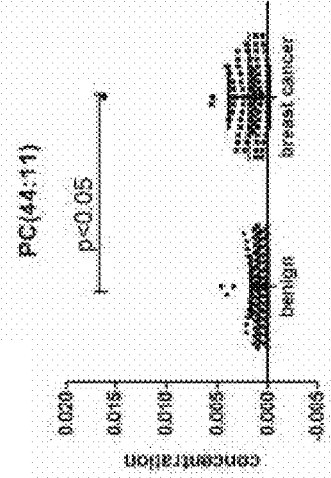

LIPID MARKERS FOR EARLY DIAGNOSIS OF BREAST CANCER

RELATED APPLICATIONS

This application claims the benefit of U.S. Provisional Application No. 62/408,410, filed Oct. 14, 2016, which is incorporated by reference herein its entirety.

TECHNICAL FIELD

The present invention relates to methods for diagnosing breast cancer, and in particular to methods for diagnosing breast cancer using a panel of lipid biomarkers for diagnosing breast cancer.

BACKGROUND

Breast cancer is the most frequently diagnosed cancer and the second leading causes of cancer-related death among women in the United States [1]. According to the American Cancer Society (ACS) estimation in 2015, 231,840 new breast cancer cases were diagnosed, which accounts for 29% of all newly diagnosed female cancer patients. And 40,290 of breast cancer deaths cover 15% of cancer-related death among women [1]. Early diagnosis plays a key role in patients' prognosis. Mammography is currently the most widely used method in breast cancer scanning. However, the outcome is not satisfactory because of the high false positive rate [2].

The overdiagnosis of breast cancer in screening mammography is wide, from 0% to upwards of 30% [3]. Women with abnormal screening mammograms undergo additional expensive magnetic resonance imaging (MRI) and tissue sampling (by fine-needle aspiration, core biopsy, or excisional biopsy). Even worse, about 10% of women will be called back from each screening examination for further testing, but only 5% of these women will have cancer, and the others turn out to be benign [4]. Chiarelli et al [5] had reported that breast MRI plus mammography is an effective way for breast cancer screening. However, it is very expensive and it has not been demonstrated that screening high-risk populations with MRI has translated into a survival benefit [6]. Further, MRI has a high false-positive rate and could lead to high frequency of futile biopsies with additional stress and cost [7]. To avoid unnecessary expensive and invasive screening for those benign patients, a better method is urgently needed. Blood-based tumor marker is one of the research hotspots in diagnosis of cancers. However, they are not used in clinical trials up to-date [8-10]. Serum tumor markers such as CA15.3 and BR27.29 have low sensitivity and thus are not used for breast cancer detection [11]. Thus, there is a pressing need for minimally invasive methods and early diagnosis of malignant breast lesions.

Lipids are involved in regulating many physiological activities, such as energy storage, structure, apoptosis, and signaling [12]. Many studies have reported that, as a major component of metabolic syndrome, dyslipidemia plays an important role in the carcinogenesis of various cancers, including in prostate cancer, ovarian cancer and kidney cancer [13-15]. For breast cancer, it has been well shown that metabolomics or lipidomics had potential for cancer diagnosis and progression [16-18]. However, most of these studies have been just focused on total levels of lipids in cancer patients, and only a few of them included patients with benign breast diseases. Recently, Yang et al. performed a comprehensive evaluation of plasma lipid profiles with benign breast disease patients in only 5 breast cancer cases and 6 benign patients, indicating the diagnostic efficiency of the lipid markers in these diseases [19].

This study uses lipidomics technology and electrospray ionization tandem mass spectrometry (ESI-MS/MS) to make quantitative analysis for plasma samples in both a training set and a validation set including a total of 84 breast cancer patients and 110 benign patients. The whole set (the combined training and validation sets) was used to verify the credibility of the results. In this study a panel of plasma lipid species were identified which were able to distinguish early stage of cancer from benign lesions, and serve as potential biomarkers for early diagnosis of breast cancer.

What is needed is a biomarker panel for diagnosing breast cancer.

BRIEF SUMMARY

Methods for measuring a panel of biomarkers in a subject suspected of having breast cancer are provided. The methods include obtaining a biological sample from the subject and determining a measurement for a panel of biomarkers in the biological sample, the panel comprising at least 5 biomarkers selected from the group comprising LPC(18:3), LPC(20:2), LPC(20:1), LPC(20:0), PC(32:1), PC(34:4), PC(38:3), PC(40:5), PC(40:3), PC(44:11), ePC(32:2), ePC(38:3), C19:1 CE, C19:0 CE, and C20:0 CE, wherein the measurement comprises measuring a level of each of the at least 5 biomarkers in the panel.

In some embodiments, the methods include measuring the panel of biomarkers comprising LPC(18:3), LPC(20:2), LPC(20:1), LPC(20:0), PC(32:1), PC(34:4), PC(38:3), PC(40:5), PC(40:3), PC(44:11), ePC(32:2), ePC(38:3), C19:1 CE, C19:0 CE, and C20:0 CE.

BRIEF DESCRIPTION OF THE DRAWINGS

FIG. 2A shows LPC(18:3). FIG. 2G shows PC(38:3). FIG. 2H shows PC(40:5). FIG. 2I shows PC(40:3). FIG. 2J shows PC(44:11). FIG. 2K shows ePC(32:2). FIG. 2L shows ePC(38:3). FIG. 2O shows C20:0 CE. (Abbreviations for FIGS. 2A-2O: LPC lysophosphatidylcholine; PC phosphatidylcholine; ePC ether-linked phosphatidylcholine; CE cholesterol ester.)

FIG. 3A shows breast cancer versus benign in the training set. FIG. 3B shows breast cancer versus benign in the validation set. FIG. 3C shows breast cancer versus benign in the whole set.

DETAILED DESCRIPTION

Figure 1:
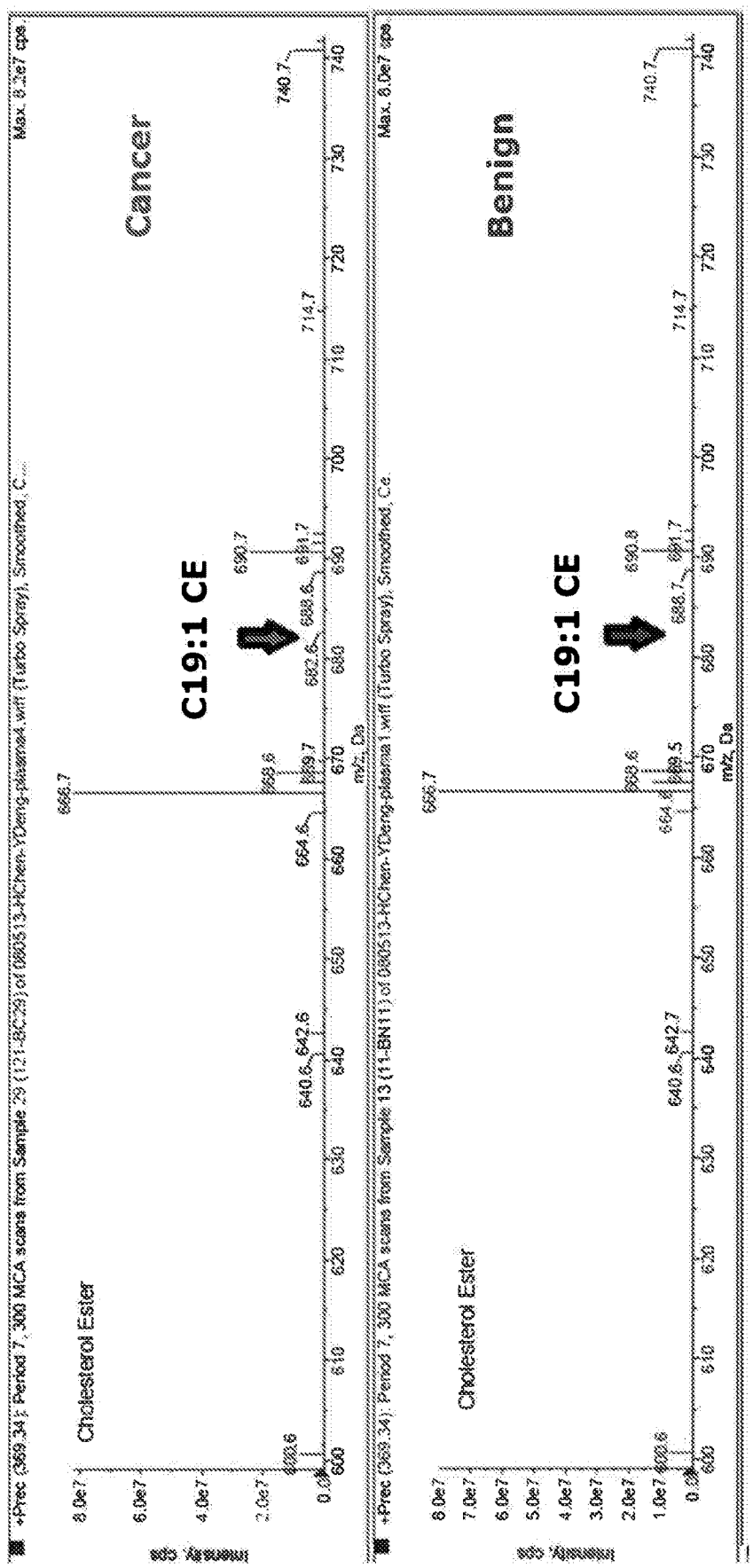
FIG. 1 illustrates the mass spectra of C19:1 CE in breast cancer and benign samples.
Figures 2A, 2B, 2C, 2D, 2E, 2F:
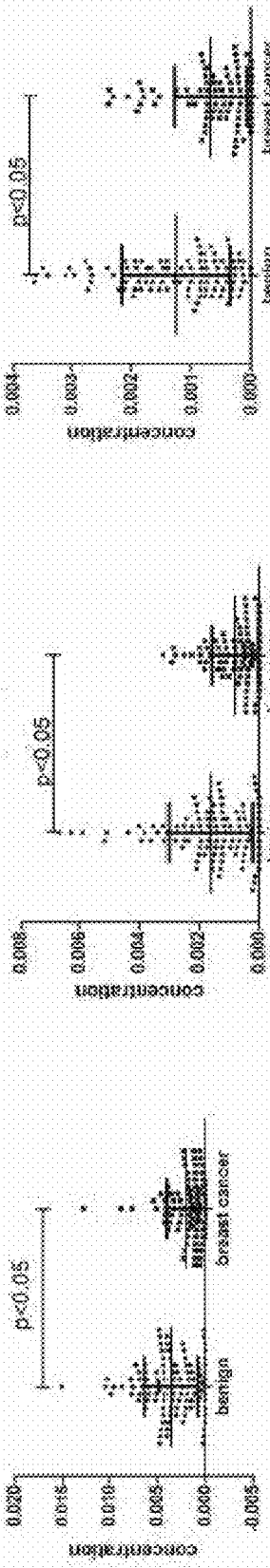
FIGS. 2A-2O illustrate the plasma concentrations of 15 lipid species of a panel of biomarkers. The black horizontal lines are median values. p values were determined by the students' T-test.
FIG. 2B shows LPC(20:2).
FIG. 2C shows LPC(20:1).
FIG. 2D shows LPC(20:0).
FIG. 2E shows PC(32:1).
FIG. 2F shows PC(34:4).
Figure 2M:
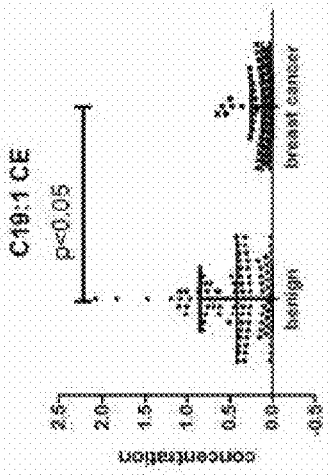
FIG. 2M shows C19:1 CE.
Figure 2N:
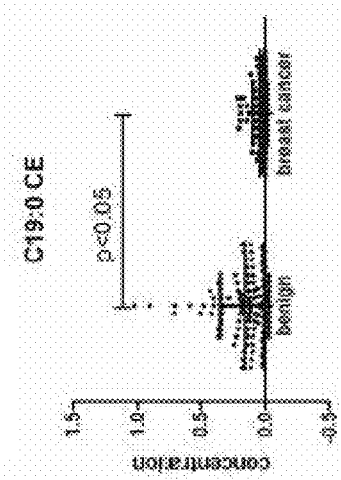
FIG. 2N shows C19:0 CE.
Figure 2O:
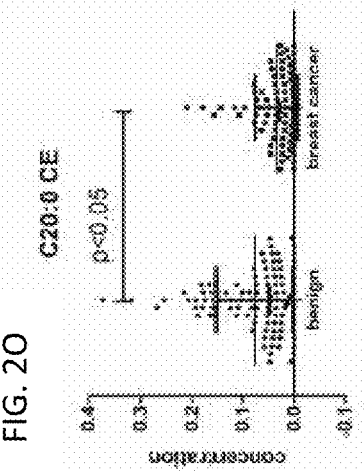

The present invention will utilize a panel of biomarkers measured in a biological sample obtained from a subject to identify subjects having breast cancer. In some embodiments, the panel of biomarkers includes lipid biomarkers.

The term "biomarker" as used herein, refers to any biological compound that can be measured as an indicator of the physiological status of a biological system. In some embodiments, the biomarker may comprise a lipid. Exemplary lipids include, but are not limited to lysophosphatidylcholnes (LPC), phosphatidylcholines (PC), ether-lined phosphatidylcholines (ePC) and cholesterol esters (CE).

"Measuring" or "measurement" means assessing the presence, absence, quantity or amount (which can be an effective amount) of a given substance within a sample, including the derivation of qualitative or quantitative concentration levels of such substances, or otherwise evaluating the values or categorization of a subject's clinical parameters. Alternatively, the term "detecting" or "detection" may be used and is understood to cover all measuring or measurement as described herein.

The terms "sample" or "biological sample" as used herein, refers to a sample of biological fluid, tissue, or cells, in a healthy and/or pathological state obtained from a subject. Such samples include, but are not limited to, blood, bronchial lavage fluid, sputum, saliva, urine, amniotic fluid, lymph fluid, tissue or fine needle biopsy samples, peritoneal fluid, cerebrospinal fluid, nipple aspirates, and includes supernatant from cell lysates, lysed cells, cellular extracts, and nuclear extracts. In some embodiments, the whole blood sample is further processed into serum or plasma samples.

The term "subject" as used herein, refers to a mammal, preferably a human.

Biomarker Panel

Biomarkers that may be used include but are not limited to lipids. In some embodiments, the biomarkers may be lipids that are circulating in the subject that may be detected from a fluid sample obtained from the subject.

In some embodiments, the biomarker panel may include 2, 3, 4, 5, 6, 7, 8, 9, 10, 11, 12, 13, 14 or 15 biomarkers. In some embodiments, the biomarker panel may include ten or fewer biomarkers. In yet other embodiments, the biomarker panel may include 2, 3, 6 or 7 biomarkers. In some embodiments, the biomarker panel may include 15 biomarkers. In some embodiments, the biomarker panel may be optimized from a candidate pool of biomarkers. By way of non-limiting example, the biomarker panel may be optimized for determining whether a subject has a breast cancer. The biomarker panel may be optimized for differentiating between breast cancer and benign disease using a candidate biomarker panel starting with fifteen candidate biomarkers selected from the group including LPC(18:3), LPC(20:2), LPC(20:1), LPC(20:0), PC(32:1), PC(34:4), PC(38:3), PC(40:5), PC(40:3), PC(44:11), ePC(32:2), ePC(38:3), C19:1 CE, C19:0 CE, and C20:0 CE.

Biomarker Panel Measurement

Measurement of a biomarker panel generally relates to a quantitative measurement of a plurality of lipid biomarkers. The measurement of the biomarker panel of the subject detects differences in lipid concentrations in subjects having breast cancer compared to subjects that are free from breast cancer. The concentration of each individual biomarker may be higher or lower in the subjects having breast cancer compared to subjects that are free from cancer. A panel of a plurality of biomarkers provides an improved predictive value relative to a single biomarker.

Measurement of the biomarkers may be measured using any method known to one skilled in the art. Methods for measuring lipids include, but are not limited to spectrometric methods including soft ionization techniques for mass spectrometry such as electrospray ionization (ESI) and matrix-assisted laser desorption/ionization (MALDI). In some embodiments a triple quadrupole Liquid chromatography electrospray ionization tandem mass spectrometry (LC-ESI-MS/MS) may be used. Lipids from the panel of biomarkers are measured in the subject and compared to the levels of the panel of biomarkers obtained from a cohort of subjects described below.

Analysis of Biomarker Panel Measurements

In some embodiments, methods of determining whether a subject has breast cancer are based upon the biomarker panel measurement compared to a reference profile that can be made in conjunction with statistical analysis. In some embodiments SPSS software may be used for the statistical analyses. In some embodiments, binary logical regression analysis may be used to predict the diagnostic efficiency of the selected lipid species. In some embodiments, a statistical algorithm used with a computer to implement the statistical algorithm to sort the subject into a group may be used. In some embodiments, the statistical algorithm is a learning statistical classifier system. The learning statistical classifier system can be selected from the following list of non-limiting examples, including Random Forest (RF), Classification and Regression Tree (CART), boosted tree, neural network (NN), support vector machine (SVM), general chi-squared automatic interaction detector model, interactive tree, multiadaptive regression spline, machine learning classifier, and combinations thereof.

In some embodiments, the biomarker panel has a sensitivity of at least 80%. In some embodiments, the biomarker panel has a specificity of at least 80%, at least 85% or at least 90%. In some embodiments, the biomarker panel has a positive predictive value of at least 80%, or at least 85%. In some embodiments, the biomarker panel has a negative predictive value of at least 80%, or at least 85%.

Treatment Stratification

In some embodiments, the analysis of the biomarker panel may be used to determine a treatment regime for the subject. In some embodiments, the measurement of one or more biomarkers in the panel may be used to determine whether to begin a treatment, to continue the same treatment or to modify the treatment regime for a subject. In some embodiments, the analysis of the biomarker panel may determine that the subject does not have breast cancer and no treatment may be initiated. In some embodiments, the analysis of the biomarker panel may determine that the subject has breast cancer and further testing may be initiated or a treatment may be started. Treatments may include, but are not limited to chemotherapy, radiation therapy, biologic therapy, surgery and combinations thereof. In some embodiments, the treatment may be modified by changing the drug administered to the subject or to add an additional drug to the existing drug treatment regime, to change the dosage or other changes. In some embodiments, the subject with a negative result of the biomarker panel analysis may be stratified to a group for follow up testing, for example in 6-12 months.

Results

Characteristics of Patients

A total of 84 patients with early stage breast cancer (stage 0-II) and 110 with benign breast disease were included in our study. The mean age was 57.7±12.0 Years in breast cancer group, 47.8±10.9 in the benign group. Among these patients, the breast cancer group had 79 (94%) caucasians and 5 (6%) non-caucasians. In the benign group, there were 103 (94%) caucasians and 7 (6%) non-caucasians. Therefore, most of the patients were caucasians in our study (>90%). The stage of the breast cancer was as follow: 15 (18%) patients was stage 0, 58 (69%) patients was stage I, and 11 (13%) patients was stage II. According to the samples from different departments, the breast cancer and benign sample were divided into a training set of 90 patients and a validation set of 94 patients. The training and validation set samples were approximately age- and race-matched. The details were showed in Table 1.

Lipid Profiling of Lipid Species

Plasma lipid profiles including 367 lipid species from 13 classes of phospholipids and 1 class of CE were identified by lipidomics from a total of 194 plasma samples (84 with breast cancer and 110 with benign breast disease). Due to our test utilized the method of lipid micro-extraction, the level of lipid species less than 0.0007 nmol/uL was considered likely unreliable. In order to guarantee the quality of lipid species, we removed lipids with more than 40% missing data or outlier mean expression. Therefore, 367 lipid species were reduced to 191 lipid species. As an example, the mass spectra of C19:1 CE was shown in FIG. 1 for a patient with breast cancer and a patient with benign breast disease.

The concentration of lipid species from both breast cancer and benign plasma specimens were analyzed. In the training set, the most significant difference in mean plasma concentration was PC (38:3) ($p=2.50297E-08$, Student's t-test). The significant fold change was LPC (20:0) (fold-change=4.08). In the validation set, the most significant difference in mean plasma concentration was PC (38:3) ($p=5.70481E-11$, Student's t-test). The significant fold change was C 19:0 CE (fold-change=4.39). In the whole set (the combined training and validation sets), the most significant difference in mean plasma concentration was PC (38:3) ($p=1.00749E-17$, Student's t-test). The significant fold change was C 19:0 CE (fold-change=3.73). These data indicated that plasma lipid species could be the biomarkers for the diagnosis of breast cancer.

Identification of Lipid Species as Biomarkers for Early Stage Breast Cancer

The change in the concentration of 191 lipid species in the training set was analyzed. The p value of the Student's t-test and the fold-change of the average of the concentration of each lipid species were calculated between breast cancer samples and benign samples. According to the filtering condition ($p<0.05$ and fold change$>1.5$), only 15 lipid species were selected as biomarkers for diagnosis of breast cancer (Table 2). The concentration distribution of these selected lipid species was shown in FIG. 2. Among these 15 lipid species, there were 4 LPC, 6 PC, 2 ePC, and 3 CE species (Table 2). Compared to that in benign patients, the plasma concentration of the two classes of LPC and CE were observed decreased in cancer patients, while the other lipid species increased (Table 2).

Figure 3A:
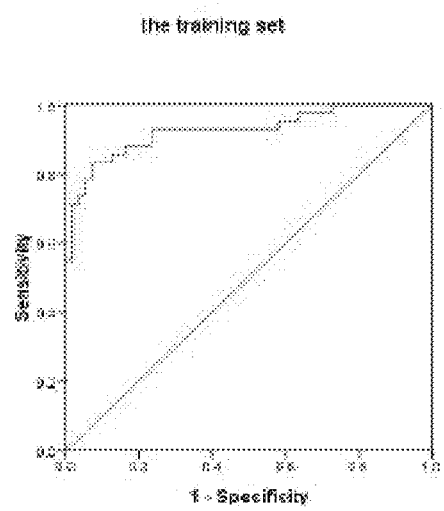
FIGS. 3A-3C show ROC curves of a panel of 15 lipid biomarkers for prediction of breast cancer. The panel of 15 lipid biomarkers are identified in FIGS. 2A-2O.

To test the prediction value of the 15 selected lipids for breast cancer, a binary logistic regression was used to build prediction model. According to the prediction model, we could further evaluate the performance of the selected lipid species in distinguishing breast cancer patients from benign patients. We found that single lipid species did not have good diagnostic performance in distinguishing breast cancer patients from benign patients. However, the combination of these 15 lipid species had the best diagnostic performance. The sensitivity, specificity, positive predictive value (PPV) and negative predictive value (NPV) of the combination these 15 lipid species were 83.3%, 92.7%, 89.7%, and 87.9%, respectively. The AUC was 0.926 (95% CI 0.869-0.982) (FIG. 3 A).

Figure 3B:
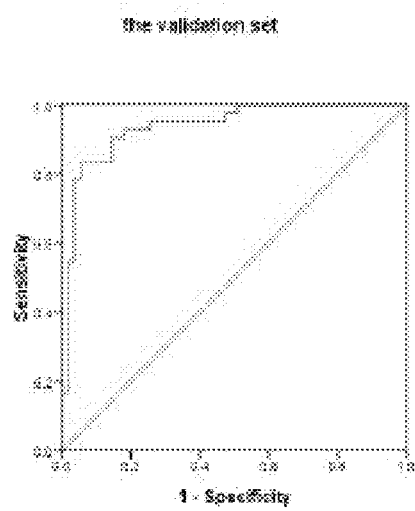
Figure 3C:
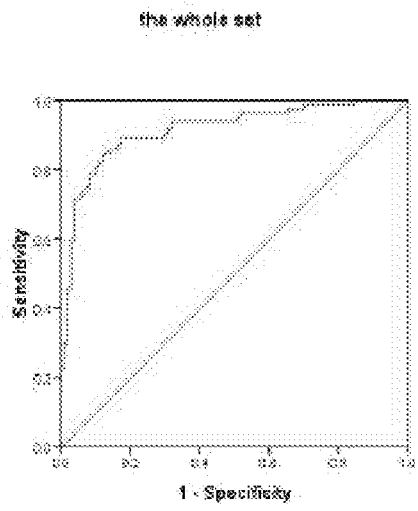

In order to further verify these 15 lipid species as potential biomarkers in diagnosis of breast cancer, we used the same method to analyze the data of the validation set (Table 2). The similar results were found in the validation set. The sensitivity, specificity, PPV and NPV were 81.0%, 94.5%, 91.9%, and 86.7%, respectively. The AUC were 0.938 (95% CI 0.889-0.986) (FIG. 3B). In the whole set (the combination of the training set and the validation set), the sensitivity, specificity, PPV and NPV were 81.0%, 90.0%, 86.1%, and 86.1%, respectively (AUC 0.916, 95% CI 0.874-0.957) (FIG. 3C).

DISCUSSION

Breast cancer is very common and highly fatal in women. Mammography is currently used in breast cancer screening, with the sensitivity merely at 54% to 77% [20]. Most abnormal mammograms are false positives that require further investigations including expensive breast imaging and biopsies, which can cause physiological distress. Due to the limitation of mammography, radiological interpretation of indeterminate micro-calcifications as benign or malignant may be unreliable [21]. Thus, the new diagnostic technique with high accuracy for the diagnosis of breast cancer, especially for distinguishing early cancer from benign lesions, is still needed in clinical practice.

Lipids may be broadly defined as hydrophobic or amphipathic small molecules that originate entirely or in part by carbanion-based condensations of thioesters and/or by carbocation-based condensations of isoprene units [22]. Lipids have been implicated as playing roles in several human diseases, including breast cancer [23]. In particular, complex polar lipids may participate in oncologic processes, including breast cancer development and metastasis [16]. In our study, 15 lipid species were identified showing significant differences of plasma concentration between breast cancer and benign patients. The plasma concentrations of PC and ePC classes were to increase in the breast cancer patients, while the others were decreased. These results might be caused by the regulation mechanisms of cellular metabolism. PCs, which were known as the major phospholipids found in the membranes of mammalian cells, were mediated by phospholipase A2 (PLA2) in breast cancer cells [24]. Some studies had reported that PLA2 is over-expressed in breast cancer cells [25-27]. The level of the PCs may reflect a higher activity of PLA2. The ePCs belong to the subclasses of PCs, and ePCs activate PI-3-kinase and may participate in mitogenic responses [28]. LPCs and CEs were derived from PCs [29]. The decreased levels of LPCs were associated with an activated inflammatory status in cancer patients [30]. LPCs not only have inflammatory activities, but also activate signaling molecules including tyrosine kinases [31-33]. The binding of LPCs to their receptors may regulate signaling pathways including inflammation and cell migration [31, 34-35]. The lower levels of LPCs may reflect a higher metabolism rate in breast cancer patients. The metabolic effect of CE in breast cancer remains poorly understood. But the relation between CE and poor clinical outcome in human breast cancer had been reported [36]. These studies indicated that these selected lipid species could be classified as biomarkers for diagnosis of breast cancer.

Our current data showed that single plasma lipid species was unlikely to perform well in distinguishing breast cancer from benign patients. But the combination of the selected lipid species had a high diagnostic value for breast cancer prediction with high sensitivity, specificity, PPV, NPV and AUC, as shown in the training set, the validation set, and the whole set. Furthermore, the specificity of the combination of 15 selected lipid species for breast cancer (the training set:

92.7%, the validation set: 94.5%) was higher than mammograms, suggesting that these lipid markers would be potential biomarkers for diagnosis of breast cancer among women with abnormal mammograms.

As far as we known, this is the first study on plasma lipid biomarkers in distinguishing early-stage breast cancer from benign lesion in a large sample set. Our aim is to identify circulating lipid signatures that can be used reliably as a companion diagnostic tool together with screening mammography, to reduce the number of unnecessary follow-up investigations, especially invasive biopsy. Using a triple quadrupole LC-ESI-MS/MS, the lipid profiling could get the fast, high efficiency and high throughput detection. The test only required 3 uL of plasma, which was minimally invasive procedure. After biostatistical analysis, a highly sensitive and specific prediction model was acquired for the diagnosis of breast cancer. The cost of the detection of global lipid profiling is high. However, measurement of a panel of 3-15 plasma lipid species may be feasible in clinical laboratories. For that reasons, the selected lipid species were as diagnostic biomarkers only, but not as screening biomarkers.

There were some limitations in our study. First, the benign group was included many benign disease, such as hyperplasia, fibroadenomas, cysts and some unspecified findings diagnosed at this organ. According to the small sample size for each benign disease, we could not conduct the subgroup analysis. Second, most of the patients in our study were caucasian (>90%). Third, due to the incomplete information on the tumor size, we were unable to conduct correlational analysis between the lipid species and tumor size.

CONCLUSION

This study assessed the combination of lipid species as a panel for the diagnosis of breast cancer. Our findings indicate that a procedure using biostatistical analysis on a lipid profile is capable of producing a highly sensitive and specific prediction model that classifies patients between benign and malignant breast cancer. These results showed that lipid profiles may be a promising avenue to investigate diagnostic biomarkers toward breast cancer.

Materials and Methods

Patients and Plasma Samples Collection

The training cohort included 39 Breast cancer and 51 benign samples, which were obtained from the Rush Breast Cancer Repository. The patients were selected as the following criteria: (1) all patients were diagnosed and confirmed by pathology; (2) patients with breast cancer were at early stages (stage 0, I, II) according the clinical staging method; (3) patients had no other diseases which might affect lipid metabolism such as hyperlipidemia, diabetes, and other cancers; (4) all patients were female; (5) none of the patients received preoperative adjuvant chemotherapy or radiotherapy. Breast benign lesions are defined as hyperplasia, fibroadenomas, cysts and some unspecified findings diagnosed at this organ. Control blood samples were collected from healthy women with no history of malignant diseases and no inflammatory conditions.

According to these criteria, plasma samples were collected from 45 patients with early breast cancer (stage 0-II) and 59 patients with benign breast disease from The Cooperative Human Tissue Network (CHTN) Western Division and Southern Division. All cancer patient histopathology results were confirmed by surgical resection of the tumors and clinicohistopathological characteristics and tumor stage were assessed based on histobiopsy results. No preoperative chemotherapy or radiotherapy was applied to cancer patients included in this study. All these cancer, benign and control samples were approximately age- and race-matched, as shown in Table 1. Rush University Medical Center IRB gave approval on the study with written consent for using all the subject information and biospecimens.

Before collection of plasma samples, patients were fasted at least 12 hours. Briefly, for plasma isolation, blood was collected into Vacutainer tubes with EDTA (BD, Franklin Lakes, N.J.) was centrifuged at 2,600 g for 10 minutes at 4° C. within 2 hours of venipuncture. The supernatant was removed, centrifuged in the same way for the second time, and plasma was stored in 0.5 mL aliquots at −80° C. All plasma samples were transported to the Kansas Lipidomics Research Center (KLRC) for lipid analysis with dry ice.

LC-ESI-MS/MS Lipid Profiling

According to the method of Bligh and Dyer [37], the lipids were extracted from plasma with some modifications. 3 µL of plasma was used for each sample analysis. Each sample was centrifuged at 10,000 rpm for 20 minutes at room temperature on a table tube unit for pelleting the proteins before detecting. In order to obtain exact identification of all lipid species, precise amounts of internal standards were added. Two internal standards were used for each class of lipid species. After centrifuging, the lipid extracts were redissolved in the solvents for HPLC injection. The solvents were the rate of chloroform/methanol/300 mM ammonium acetate in water (µL) was 360/840/44. All solvents used were HPLC grade.

Lipid profiling was performed by a triple quadrupole LC-ESI-MS/MS (API 4000, Applied Biosystems, Foster City, Calif.), which was based on collision-induced dissociation (CID) for structural identification. The sample introduction is continuous injection of electrospray ionization (ESI) source. It could reduce the ionization suppression effect caused by spectral congestion [38]. ESI of complex lipids generates singly charged ions that can produce fragments by CID. With the help of LC-ESI-MS/MS, lipids can be distinguished by their polar heads and their chain lengths.

Lipid data acquisition was carried out as described previously [39-42]. Two types of scans are used to obtain polar lipid profiles: precursor and neutral loss scans. Lipid species in a class are identified as precursors of, or as ions that undergo neutral loss of, a common head group fragment. A custom script and Applied Biosystems Analyst software were used for the resolution of chromatographic peaks. After mass filtering, alignment, internal standard normalization, the data were quantified in the unit of nmol/µL.

Statistics Analysis

SPSS 17.0 software was used for statistical analyses. The differences between the two plasma sample sets were evaluated by the Student's t-test. All p values were derived from two-sided test. Differences were considered statistically significant when p values were less than 0.05 and fold-change was larger than 1.5.

Further statistical analysis was performed with SPSS software. According to the binary logical regression analysis, we could predict the diagnostic efficiency of the selected lipid species. The "Enter" method was chosen to estimate the diagnostic accuracy of lipid. Receiver operating characteristic (ROC) curves were plotted to assess the relation of sensitivity and specificity. Area under ROC curve (AUC) with 95% confidence interval (CI) was also calculated. Scatter plots were generated by GraphPad Prism version 5 for Windows.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

[1] Siegel R L, Miller K D, Jemal A. Cancer statistics, 2015. CA Cancer J Clin. 2015; 65(1):5-29.
[2] Gotzsche P C, Jorgensen K J. Screening for breast cancer with mammography. *Cochrane Database Syst Rev.* 2013; 6:CD001877.
[3] Morris E, Feig S A, Drexler M, Lehman C. Implications of Over diagnosis: Impact on Screening Mammography Practices. Popul Health Manag. 2015; 18Suppl 1:S3-S11.
[4] Rosenberg R D, Yankaskas B C, Abraham L A, Sickles E A, Lehman C D, Geller B M, Carney P A, Kerlikowske K, Buist D S, Weaver D L, Barlow W E, Ballard-Barbash R. Performance benchmarks for screening mammography. Radiology. 2006; 241(1):55-66.
[5] Chiarelli A M, Prummel M V, Muradali D, Majpruz V, Horgan M, Carroll J C, Eisen A, Meschino W S, Shumak R S, Warner E, Rabeneck L. Effectiveness of Screening With Annual Magnetic Resonance Imaging and Mammography: Results of the Initial Screen From the Ontario High Risk Breast Screening Program. J Clin Oncol. 2014; 32(21):2224-30.
[6] Morrow M, Waters J, Morris E. MRI for breast cancer screening, diagnosis, and treatment. Lancet. 2011; 378: 1804-1811.
[7] Yahalom J. Evidence-based breast cancer screening guidelines for women who received chest irradiation at a young age. J Clin Oncol. 2013; 31(18):2240-2.
[8] Atahan K, Küpeli H, Gür S, Yiğitbaşı T, Baskın Y, Yiğit S, Deniz M, Cökmez A, Tarcan E. The value of serumbiomarkers (Bc1, Bc2, Bc3) in the diagnosis of early breast cancer. *Int J Med Sci.* 2011; 8(2):148-155.
[9] Donepudi M S, Kondapalli K, Amos S J, Venkanteshan P. Breast cancer statistics and markers. *J Cancer Res Ther.* 2014; 10(3):506-511.
[10] Misek, D. E.; Kim, E. H. Protein biomarkers for the early detection of breast cancer. Int J Proteomics 2011, 2011:343582.
[11] Molina R, Barak V, van Dalen A, Duffy M J, Einarsson R, Gion M, Goike H, Lamerz R, Nap M, Sölétormos G, Stieber P. Tumor markers in breast cancer-European Group on Tumor Markers recommendations. Tumour Biol. 2005; 26(6):281-293.
[12] Gross R W, Han X L. Lipidomics at the interface of structure and function in systems biology. Chem Biol. 2011; 18(3):284-291.
[13] Zhang G M, Qin X J, Zhang H L, Xiao W J, Zhu Y, Gu C Y, Dai B, Shi G H, Ye D W. Serum lipid profiles: novel biomarkers predicting advanced prostate cancer in patients receiving radical prostatectomy. Asian J Androl. 2015; 17(2):239-244.
[14] Liu Y, Chen Y, Momin A, Shane R, Wang E, Bowen N J, Matyunina L V, Walker L D, McDonald J F, Sullards M C, Merrill A H Jr. Elevation of sulfatides in ovarian cancer: an integrated transcriptomic and lipidomic analysis including tissue-imaging mass spectrometry. Mol Cancer. 2010; 9:186.
[15] Cífková E, Holčapek M, Lisa M, Vrána D, Melichar B, Student V. Lipidomic differentiation between human kidney tumors and surrounding normal tissues using HILIC-HPLC/ESI-MS and multivariate data analysis. *J Chromatogr B Analyt Technol Biomed Life Sci.* 2015; 1000: 14-21.
[16] Min H K, Kong G, Moon M H. Quantitative analysis of urinary phospholipids found in patients with breast cancer by nanoflow liquid chromatography-tandem mass spectrometry: II. Negative ion mode analysis of four phospholipid classes. Anal Bioanal Chem. 2010; 396(3):1273-1280.
[17] Qiu Y, Zhou B, Su M, Baxter S, Zheng X, Zhao X, Yen Y, Jia W. Mass spectrometry-based quantitative metabolomics revealed a distinct lipid profile in breast cancer patients. Int J Mol Sci. 2013; 14(4):8047-8061.
[18] Hilvo M, Denkert C, Lehtinen L, Müller B, Brockmöller S, Seppänen-Laakso T, Budczies J, Bucher E, Yetukuri L, Castillo S, Berg E, Nygren H, Sysi-Aho M, Griffin J L, Fiehn O, Loibl S, Richter-Ehrenstein C, Radke C, Hyötyläinen T, Kallioniemi O, Iljin K, Oresic M. Novel theranostic opportunities offered by characterization of altered membrane lipid metabolism in breast cancer progression. Cancer Res. 2011; 71(9):3236-3245.
[19] Yang L, Cui X, Zhang N, Li M, Bai Y, Han X, Shi Y, Liu H. Comprehensive lipid profiling of plasma in patients with benign breast tumor and breast cancer reveals novel biomarkers. Anal Bioanal Chem. 2015; 407(17):5065-5077.
[20] Guth U, Huang D J, Huber M, Schotzau A, Wruk D, Holzgreve W, Wight E, Zanetti-Dallenbach R. Tumor size and detection in breast cancer: Self-examination and clinical breast examination are at their limit. Cancer detection and prevention. 2008, 32(3):224-228.
[21] Burrell H C, Evans A J, Wilson A R, Pinder S E. False-negative breast screening assessment: what lessons can we learn? Clin Radiol. 2001; 56(5):385-358.
[22] Fahy E, Subramaniam S, Murphy R C, Nishijima M, Raetz C R, Shimizu T, Spener F, van Meer G, Wakelam M J, Dennis E. A. Update of the LIPID MAPS comprehensive classification system for lipids. *J Lipid Res.* 2009; 50 Suppl:S9-14.
[23] Hietanen E, Punnonen K, Punnonen R, Auvinen O. Fatty acid composition of phospholipids and neutral lipids and lipid peroxidation in human breast cancer and lipoma tissue. Carcinogenesis. 1986; 7(12):1965-1969.
[24] You J, Yang J, Fang R, Hu N, Zhang X, Zhang W, Ye L. Analysis of Phosphatidylcholines (PCs) and Lysophosphatidylcholines (LysoPCs) in Metastasis of Breast Cancer Cells. Progress in Biochemistry and Biophysics. 2015; 42(6): 563-573.
[25] Dong Q, Patel M, Scott K F, Graham G G, Russell P J, Sved P. Oncogenic action of phospholipase A2 in prostate cancer. Cancer Lett. 2006; 240(1):9-16.
[26] Laye J P, Gill J H. Phospholipase A2 expression in tumours: A target for therapeutic intervention? Drug Discov Today. 2003; 8(15):710-716.
[27] Yamashita S, Yamashita J, Sakamoto K, Inada K, Nakashima Y, Murata K, Saishoji T, Nomura K, Ogawa M. Increased expression of membrane-associated phospholipase A2 shows malignant potential of human breast cancer cells. Cancer. 1993; 71(10):3058-3064.
[28] Misra S, Ghosh A, Varticovski L. Naturally occurring ether-linked phosphatidylcholine activates phosphatidylinositol 3-kinase and stimulates cell growth. J Cell Biochem. 1994; 55(1):146-153.
[29] Sekas G, Patton G M, Lincoln E C, Robins S J. Origin of plasma lysophosphatidylcholine: evidence for direct hepatic secretion in the rat. J Lab Clin Med. 1985; 105(2):190-194.

[30] Taylor L A, Arends J, Hodina A K, Unger C, Massing U. Plasma lysophosphatidylcholine concentration is decreased in cancer patients with weight loss and activated inflammatory status. Lipids Health Dis. 2007; 6:17.
[31] Qin X, Qiu C, Zhao L. Lysophosphatidylcholine perpetuates macrophage polarization toward classically activated phenotype in inflammation. Cellular immunology. 2014: 289: 185-90.
[32] Carneiro A B, Iaciura B M, Nohara L L, Lopes C D, Veas E M, Mariano V S, Bozza P T, Lopes U G, Atella G C, Almeida I C, Silva-Neto M A. Lysophosphatidylcholine triggers TLR2- and TLRr-mediated signaling pathways but counteracts LPS-induced NO synthesis in peritoneal macrophages by inhibiting NF-kappaB translocation and MAPK/ERK phosphorylation. PloS one. 2013: 8:e76233.
[33] Wuhnaqimuge, Itakura A, Matsuki Y, Tanaka M, Arioka M. Lysophosphatidylcholine enhances NGF-induced MAK and AKt signals through the extracellular domain of TrkA in PC12 cells. FEBS open bio. 2013: 3: 243-251.
[34] Monet M, Gkika D, Lehen'kyi V, Pourtier A, Vanden Abeele F, Bidaux G, Juvin V, Rassendren F, Humez S, Prevarsakaya N. Lysophospholipids stimulate prostate cancer cell migration via TRPV2 channel activation. Biochimica et biophysica acta. 2009: 1793:528-39.
[35] Tan M, Hao F, Xu X, Chisolm G M, Cui M Z. Lysophosphatidylcholine activates a novel PKD2-medicated signaling pathway that controls monocyte migration. Arteriosclerosis, thrombosis, and vascular biology. 2009: 29: 1376-82.
[36] de Gonzalo-Calvo D, López-Vilaró L, Nasarre L, Perez-Olabarria M, Vázquez T, Vázquez T, Badimon L, Barnadas A, Lerma E, Llorente-Cortés V. Intratumor cholesteryl ester accumulation is associated with human breast cancer proliferation and aggressive potential: a molecular and clinicopathological study. BMC Cancer. 2015; 15:460.
[37] Bligh E G, Dyer W J. A rapid method of total lipid extraction and purification. Can J Biochem Physiol. 1959; 37(8):911-917.
[38] Taguchi R, Houjou T, Nakanishi H, Yamazaki T, Ishida M, Imagawa M, Shimizu T. Focused lipidomics by tandem mass spectrometry. J Chromatogr B Analyt Technol Biomed Life Sci. 2005; 823(1):26-36.
[39] Yang K, Jenkins C M, Dilthey B, Gross R W. Multi-dimensional mass spectrometry-based shotgun lipidomics analysis of vinyl ether diglycerides. Anal Bioanal Chem. 2015; 407(17):5199-5210.
[40] Anesi A, Guella G. A fast liquid chromatography-mass Spectrometry methodology for membrane lipid profiling through hydrophilic interaction liquid chromatography. J Chromatogr A. 2015; 1384:44-52.
[41] Zhang T, Chen S, Liang X, Zhang H. Development of a mass-spectrometry-based lipidomics platform for the profiling of phospholipids and sphingolipids in brain tissues. Anal Bioanal Chem. 2015; 407(21):6543-6555.
[42] Zhou X, Mao J, Ai J, Deng Y, Roth M R, Pound C, Heneqar J, Welti R, Bigler S A. Identification of plasma lipid biomarkers for prostate cancer by lipidomics and bioinformatics. PloS One. 2012; 7(11):e48889.

TABLE 1

The characteristics of the patients with cancer and benign lesion in the training and validation set

| | Rush Training set | | CHTN Validation set | |
|---|---|---|---|---|
| | Cancer (39) | Benign (51) | Cancer (45) | Benign (59) |
| Gender | | | | |
| Female | 39 | 51 | 45 | 59 |
| Age range (years, mean ± SD) | 57.5 ± 12.0 | 59.8 ± 11.1 | 58.0 ± 12.4 | 62.1 ± 11.1 |
| Race | | | | |
| Caucasian | 37 | 49 | 42 | 54 |
| Non-caucasian | 2 | 2 | 3 | 5 |
| Cancer stage | | | | |
| 0 | | 6 | | 9 |
| I | | 27 | | 31 |
| II | | 6 | | 5 |
| Cancer subtypes | | | | |
| Invasive | | 33 | | 35 |
| In situ | | 6 | | 10 |

SD: standard deviation.

TABLE 2

The detection of lipid species as potential biomarkers for diagnosis of early stage breast cancer.

| | | | | Training set | | | | | |
|---|---|---|---|---|---|---|---|---|---|
| Lipid species | Formula | P value | Fold-change | SN (%) | SP (%) | PPV (%) | NPV (%) | AUC (95% CI) | Trend (Cancer) |
| LPC(18:3) | 026H48O7PN | 0.0001 | 1.73 | 61.9 | 70.9 | 61.9 | 70.9 | 0.326(0.213-0.439) | down |
| LPC(20:2) | 028H54O7PN | 0.000867 | 2.19 | 64.3 | 67.3 | 60.0 | 71.2 | 0.320(0.213-0.426) | down |
| LPC(20:1) | 028H56O7PN | 0.002848 | 2.13 | 64.3 | 70.9 | 62.8 | 72.2 | 0.269(0.169-0.370) | down |
| LPC(20:0) | 028H58O7PN | 0.000183 | 4.08 | 73.8 | 65.5 | 62.0 | 76.6 | 0.289(0.186-0.392) | down |
| C19:1 CE | C46H84NO2 | 1.31E−05 | 3.17 | 71.4 | 67.3 | 62.5 | 75.5 | 0.270(0.166-0.374) | down |
| C19:0 CE | C46H86NO2 | 0.000285 | 3.24 | 71.4 | 69.1 | 63.8 | 76.0 | 0.286(0.184-0.388) | down |
| C20:0 CE | C47H88NO2 | 0.000436 | 2.09 | 57.1 | 74.5 | 63.2 | 69.5 | 0.303(0.196-0.410) | down |
| PC(32:1) | C40H78O8PN | 4.46E−06 | 1.97 | 52.4 | 83.6 | 81.0 | 69.7 | 0.776(0.680-0.871) | up |
| PC(34:4) | C42H76O8PN | 3.84E−08 | 1.84 | 57.1 | 85.5 | 75.0 | 72.3 | 0.824(0.740-0.907) | up |
| PC(38:3) | C46H86O8PN | 2.5E−08 | 1.70 | 54.8 | 87.3 | 76.7 | 71.6 | 0.822(0.737-0.908) | up |
| PC(40:5) | C48H86O8PN | 2.92E−06 | 1.58 | 50.0 | 83.6 | 70.0 | 68.7 | 0.765(0.666-0.863) | up |
| PC(40:3) | C48H90O8PN | 9.16E−05 | 1.88 | 54.8 | 85.5 | 74.2 | 71.2 | 0.729(0.624-0.835) | up |

TABLE 2-continued

The detection of lipid species as potential biomarkers for diagnosis of early stage breast cancer.

| | | | | SN | SP | PPV | NPV | | Trend |
|---|---|---|---|---|---|---|---|---|---|
| PC(44:11) | C52H82O8PN | 0.014073 | 2.06 | 45.2 | 83.6 | 67.9 | 66.7 | 0.716(0.612-0.821) | up |
| ePC(32:2) | C40H78O7PN | 0.000226 | 1.60 | 54.8 | 89.1 | 79.3 | 72.1 | 0.731(0.625-0.837) | up |
| ePC(38:3) | C46H88O7PN | 4.32E−05 | 1.93 | 61.9 | 87.3 | 78.8 | 75.0 | 0.765(0.660-0.870) | up |
| combination | — | — | — | 83.3 | 92.7 | 89.7 | 87.9 | 0.926(0.869-0.982) | — |

SN: sensitivity; SP: specificity; PPV: positive predictive value; NPV: negative predictive value; AUC: Area under ROC curve.

| | | | | Validation set | | | | | |
|---|---|---|---|---|---|---|---|---|---|
| Lipid species | Formula | P value | Fold-change | SN (%) | SP (%) | PPV (%) | NPV (%) | AUC (95% CI) | Trend (Cancer) |
| LPC(18:3) | C26H48O7PN | 0.000725 | 1.89 | 61.9 | 72.7 | 63.4 | 71.4 | 0.314(0.208-0.421) | down |
| LPC(20:2) | C28H54O7PN | 0.006665 | 1.84 | 59.5 | 69.1 | 59.5 | 69.1 | 0.303(0.198-0.409) | down |
| LPC(20:1) | C28H56O7PN | 0.02302 | 1.65 | 54.8 | 67.3 | 56.1 | 66.1 | 0.324(0.216-0.431) | down |
| LPC(20:0) | C28H58O7PN | 0.000719 | 3.32 | 66.7 | 65.5 | 59.6 | 72.0 | 0.306(0.202-0.410) | down |
| C19:1 CE | C46H84NO2 | 2.04E−05 | 3.68 | 81.0 | 63.6 | 63.0 | 81.4 | 0.260(0.160-0.360) | down |
| C19:0 CE | C46H86NO2 | 1.12E−06 | 4.39 | 78.6 | 63.6 | 62.3 | 79.5 | 0.262(0.163-0.362) | down |
| C20:0 CE | C47H88NO2 | 0.001025 | 2.36 | 64.3 | 67.3 | 60.0 | 71.2 | 0.292(0.189-0.395) | down |
| PC(32:1) | C40H78O8PN | 0.000942 | 2.36 | 38.1 | 80.0 | 59.3 | 62.9 | 0.723(0.619-0.827) | up |
| PC(34:4) | C42H76O8PN | 9.96E−05 | 1.57 | 50.0 | 80.0 | 65.6 | 67.7 | 0.736(0.636-0.837) | up |
| PC(38:3) | C46H86O8PN | 5.7E−11 | 1.83 | 66.7 | 90.9 | 84.8 | 78.1 | 0.870(0.797-0.942) | up |
| PC(40:5) | C48H86O8PN | 1.27E−09 | 1.70 | 64.3 | 85.5 | 77.1 | 75.8 | 0.839(0.757-0.920) | up |
| PC(40:3) | C48H90O8PN | 0.000657 | 1.75 | 42.9 | 83.6 | 66.7 | 65.7 | 0.670(0.559-0.781) | up |
| PC(44:11) | C52H82O8PN | 0.000228 | 2.15 | 42.9 | 87.3 | 72.0 | 66.7 | 0.707(0.600-0.815) | up |
| ePC(32:2) | C40H78O7PN | 0.010426 | 1.60 | 42.9 | 80.0 | 62.1 | 64.7 | 0.655(0.543-0.766) | up |
| | | 6.69E−06 | 2.19 | 61.9 | 89.1 | 81.3 | 75.4 | 0.754(0.648-0.860) | up |
| Combination | — | — | — | 81.0 | 94.5 | 91.9 | 86.7 | 0.938(0.889-0.986) | — |

SN: sensitivity; SP: specificity; PPV: positive predictive value; NPV: negative predictive value; AUC: Area under ROC curve.

The invention claimed is:

1. A method for measuring a panel of biomarkers in a subject suspected of having breast cancer, the method comprising:
   obtaining a biological sample from the subject;
   determining a measurement for a panel of biomarkers in the biological sample, the panel comprising at least 10 biomarkers selected from the group consisting of LPC(18:3), LPC(20:2), LPC(20:1), LPC(20:0), PC(32:1), PC(34:4), PC(38:3), PC(40:5), PC(40:3), PC(44:11), ePC(32:2), ePC(38:3), C19:1 CE, C19:0 CE, and C20:0 CE, wherein the measurement comprises measuring a level of each of the at least 10 biomarkers in the panel.

2. The method according to claim 1, wherein the panel of biomarkers comprises 15 biomarkers.

3. The method according to claim 1, wherein a level of at least one biomarker in the panel of biomarkers is decreased relative to a level of a corresponding biomarker in a reference panel.

4. The method according to claim 3, comprising measuring the level of at least one biomarker selected from the panel consisting of LPC(18:3), LPC(20:2), LPC(20:1), LPC(20:0) C19:1 CE, C19:0 CE, and C20:0 CE and 3 additional biomarkers from the panel according to claim 1.

5. The method according to claim 1, wherein a level of at least one biomarker in the panel of biomarkers is increased relative to a level of a corresponding biomarker in a reference panel.

6. The method according to claim 1, comprising measuring the biomarker panel using Liquid chromatography electrospray ionization tandem mass spectrometry (LC-ESI-MS/MS).

7. The method according to claim 6, comprising obtaining polar lipid profiles using precursor and neutral loss scans.

8. The method according to claim 1, wherein the biological sample comprises plasma.

9. The method according to claim 1, wherein the biological sample is collected prior to chemotherapy or radiotherapy.

10. A method for measuring a panel of biomarkers in a subject suspected of having breast cancer, the method comprising:
   obtaining a biological sample from the subject;
   determining a measurement for a panel of biomarkers in the biological sample, the panel comprising 15 biomarkers selected from the group consisting of LPC(18:3), LPC(20:2), LPC(20:1), LPC(20:0), PC(32:1), PC(34:4), PC(38:3), PC(40:5), PC(40:3), PC(44:11), ePC(32:2), ePC(38:3), C10:1 CE, C19:0 CE, and C20:0 CE, the measurement comprises measuring a level of the 15 biomarkers from a)-o);
   a) measuring a level of LPC(18:3) in the biological sample;
   b) measuring a level of LPC(20:2) in the biological sample;
   c) measuring a level of LPC(20:1) in the biological sample;
   d) measuring a level of LPC(20:0) in the biological sample;
   e) measuring a level of PC(32:1) in the biological sample;
   f) measuring a level of PC(34:4) in the biological sample;
   g) measuring a level of PC(38:3) in the biological sample;
   h) measuring a level of PC(40:5) in the biological sample;
   i) measuring a level of PC(40:3) in the biological sample;
   j) measuring a level of PC(44:11) in the biological sample;
   k) measuring a level of ePC(32:2) in the biological sample;
   l) measuring a level of ePC(38:3) in the biological sample;
   m) measuring a level of C10:1 CE in the biological sample;
   n) measuring a level of C19:0 CE in the biological sample; and
   o) measuring a level of C20:0 CE in the biological sample.

* * * * *